(12) United States Patent
Carlson et al.

(10) Patent No.: US 11,419,876 B2
(45) Date of Patent: Aug. 23, 2022

(54) MIRTAZAPINE AS A PRE-SHIPPING INHIBITOR OF BOVINE RESPIRATORY DISEASE

(71) Applicant: Iowa State University Research Foundation, Inc., Ames, IA (US)

(72) Inventors: Steven Alan Carlson, Story City, IA (US); Tim Day, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 72 days.

(21) Appl. No.: 16/947,607

(22) Filed: Aug. 10, 2020

(65) Prior Publication Data

US 2021/0069206 A1 Mar. 11, 2021

Related U.S. Application Data

(60) Provisional application No. 62/896,649, filed on Sep. 6, 2019.

(51) Int. Cl.
| | | |
|---|---|---|
| *A61K 31/55* | (2006.01) | |
| *A23K 20/137* | (2016.01) | |
| *A61P 11/00* | (2006.01) | |
| *A23K 50/10* | (2016.01) | |
| *A61K 9/00* | (2006.01) | |

(52) U.S. Cl.
CPC ............ *A61K 31/55* (2013.01); *A23K 20/137* (2016.05); *A23K 50/10* (2016.05); *A61P 11/00* (2018.01); *A61K 9/0019* (2013.01); *A61K 9/0053* (2013.01)

(58) Field of Classification Search
CPC .... A61K 31/55; A61K 9/0019; A61K 9/0053; A23K 20/137; A23K 50/10; A61P 11/00
See application file for complete search history.

(56) References Cited

U.S. PATENT DOCUMENTS

| | | | |
|---|---|---|---|
| 5,658,887 | A | 8/1997 | Gisby |
| 6,281,207 | B1 | 8/2001 | Richter et al. |
| 2008/0153885 | A1 | 6/2008 | Meadows et al. |
| 2014/0271709 | A1 | 9/2014 | Eddy et al. |
| 2016/0310504 | A1 | 10/2016 | De Mari et al. |
| 2017/0274065 | A1 | 9/2017 | Peters et al. |
| 2018/0185344 | A1* | 7/2018 | Carlson ............... A61K 31/546 |
| 2018/0187263 | A1 | 7/2018 | Carlson et al. |

FOREIGN PATENT DOCUMENTS

| | | |
|---|---|---|
| CN | 103585280 A | 2/2014 |
| UA | 68200 U | 3/2012 |
| WO | 2018115432 A2 | 6/2018 |

OTHER PUBLICATIONS

Wellman et al., "Meta-analysis of treatment of cattle with bovine respiratory disease with tulathromycin", J. vet. Pharmacol. Therap., vol. 30, pp. 234-241, 2007.
International Searching Authority in connection with PCT/US2020/045597 filed Aug. 10, 2020, "The International Search Report and the Written Opinion of the International Searching Authority, or the Declaration", 21 pages, dated Nov. 18, 2020.
Wikipedia, "Bovine respiratory disease", https://en.wikIpedia.org/w/Index.php?lille=Bovlne_respiratory_disease&oldid=829504181, 4 pages, Mar. 9, 2018.
fda.gov, "REMERON (mirtazapine) Tablets", https://www.accessddata.fda.gov/drugsatfda_docs/label/2010/020415s023s024.pdf, 29 pages, 2007.

* cited by examiner

*Primary Examiner* — Snigdha Maewall
(74) *Attorney, Agent, or Firm* — McKee, Voorhees & Sease, PLC

(57) ABSTRACT

Methods for preventing feedlot bovine respiratory diseases employing mirtazapine as pre-shipment treatments are disclosed. Compositions are further disclosed. Beneficially, the methods and compositions provide safe and cost-effective management of a costly disease.

16 Claims, 1 Drawing Sheet

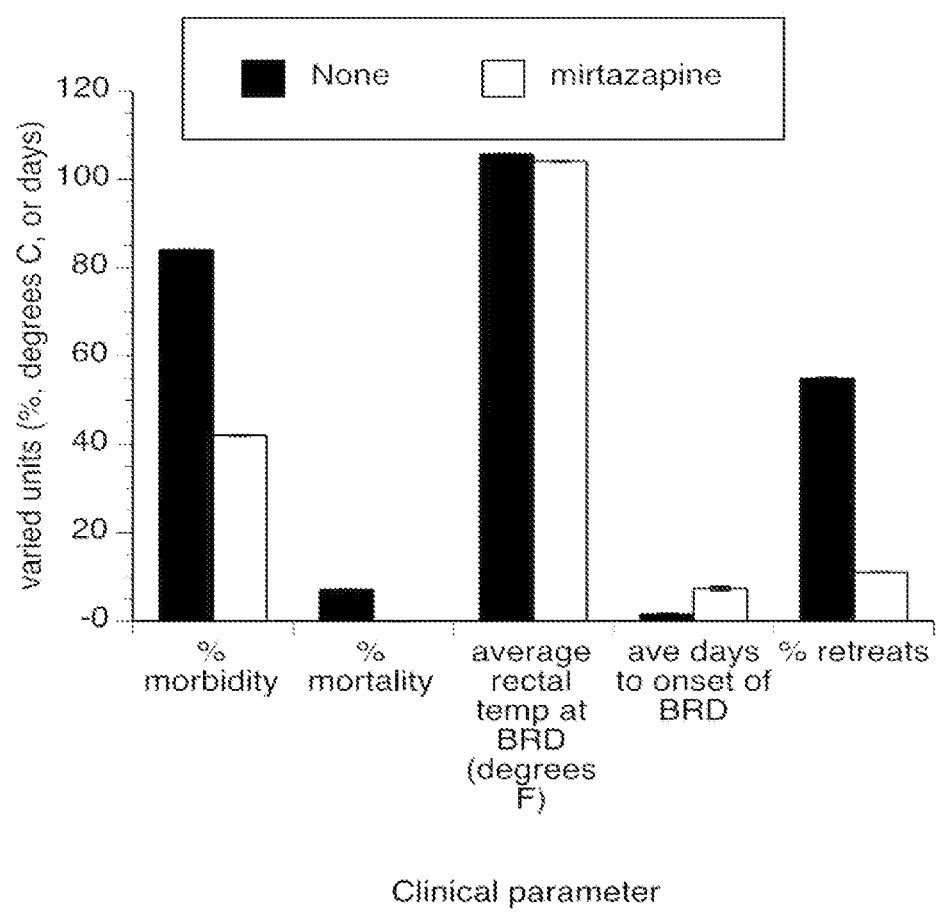

MIRTAZAPINE AS A PRE-SHIPPING INHIBITOR OF BOVINE RESPIRATORY DISEASE

CROSS-REFERENCE TO RELATED APPLICATION

This application claims priority under 35 U.S.C. § 119 to Provisional Application U.S. Ser. No. 62/896,649, filed on Sep. 6, 2019, which is herein incorporated by reference in its entirety including without limitation, the specification, claims, and abstract, as well as any FIGURES, tables, or examples thereof.

FIELD OF THE INVENTION

The present invention is related to compositions and methods for preventing feedlot bovine respiratory diseases employing mirtazapine as a pre-shipment treatment. Treatment compositions and methods comprising mirtazapine provide safe and cost effective BRD prevention, reducing the morbidity and mortality incidence of BRD and delaying onset of BRD in cattle that develop the disease which increases the survival rate.

BACKGROUND OF THE INVENTION

Bovine Respiratory Disease (BRD), a respiratory distress syndrome, is the leading cause of death in U.S. beef cattle and also the costliest disease of domestic beef cattle. BRD infection is generally understood to have three codependent factors including stress, underlying viral infection, and a bacterial infection. Key clinical signs of BRD include depression, decreasing appetite, respiratory signs, and increased temperature. BRD requires expensive treatment (estimated at least $151.18 per animal, and about $500 million per year in the U.S. and $1 billion globally) and compromises the growth of affected animals. The disease results in lost production and medical expenditures with the most recent comprehensive U.S. Department of Agriculture data published in 2013 revealing that the incidence of the disease is about 16%. Overall, the disease is estimated to cost more than $1 billion dollars in total cost per year in the U.S.

BRD is known to involve numerous bovine respiratory viruses. For example, herpesvirus-1, bovine respiratory syncytial virus, parainfluenzavirus-3, bovine coronavirus, bovine viral diarrhea virus, bovine reovirus, *Mannheimia haemolytica, Pasteurella multocida, Histophulus somni*, and *Mycoplasma bovis* have all been implicated in BRD. Vaccines are not currently effective for prevention of such viral respiratory diseases, including BRD. In addition, various bacterial pathogens are associated with BRD. Given the complex bacterial and viral etiologies involved with BRD, prevention and treatment of this disease complex is difficult. Current production management practices used by the industry only alleviate part of the problem. For example, available vaccines do not target all of the BRD-causing pathogens, and antibiotic metaphylaxis does not eliminate all BRD-causing respiratory bacteria. Moreover, the recent approval of two new BRD-targeted antibiotics (gamithromycin and tildipirosin) suggests that the currently available drugs are inadequate despite advances in antimicrobial therapy, as BRD continues to plague the cattle industry. There are also no effective broad prevention strategies currently available.

Susceptibility to BRD has been suggested in some cattle breeds, but other studies indicate that BRD susceptibility lacks a heritable genetic basis. Given the uncertainty of genotypes that determine BRD resistance or susceptibility and the overuse of metaphylactic antibiotics used versus BRD, a non-antibiotic solution and/or a non-vaccine solution is a desirable approach, each of which are objectives of the present invention. Antibiotic-independent prevention of BRD would beneficially reduce the prevalence of this costly disease, and prevention would reduce disease-associated costs and the overuse of metaphylactic antibiotics that contributes to antibiotic resistance. Being the most common disease impacting cattle in the United States, BRD affects about 10% of the more than 6 million calves transported each year. Because BRD remains the single most expensive and deadly beef cattle disease in the U.S., development of new technologies and approaches that effectively reduce BRD incidence is critical to promote both animal health and animal production. In addition, the reduction of BRD incidence would significantly decrease the over nine million doses of antibiotics are used annually to prevent these substantial deaths caused by BRD.

Accordingly, it is an objective of the invention to provide compositions for preventing feedlot bovine respiratory diseases employing the drug mirtazapine. It is also an objective of the invention to provide a method for utilizing the compositions.

Other objects, advantages and features of the present invention will become apparent from the following specification taken in conjunction with the accompanying examples or drawings.

BRIEF SUMMARY OF THE INVENTION

According to an embodiment, methods and compositions for preventing BRD using pre-shipment treatments are provided for cattle. The methods and compositions overcome shortcomings of the conventional vaccine technologies and/or antimicrobial therapies commercially available which are insufficient in preventing BRD. As no broadly effective strategy to combat this disease is currently available, the present invention provides a safe and cost effective anti-BRD drug to reduce this problem and its associated costs.

In one embodiment methods of preventing BRD in a feedlot are provided and include administering to a population of cattle in need of BRD prevention a therapeutically effective amount of mirtazapine or one of its pharmaceutically acceptable derivatives; wherein the mirtazapine is administered to the cattle before they are shipped and at a frequency and for a duration of time effective to reduce the incidence of BRD by at least 50%. In embodiments, the therapeutic agent is orally-administered and can be provided directly to the mouth of the animal or into the feed source for the animal and the dosage form is tablets, powder, capsules, solutions (aqueous or non-aqueous), suspensions, syrups, or emulsions. In embodiments, the therapeutic agent is administered by injection and can be provided in the form of a thixotropic liquid and/or injected as an implanted depot. In any of the embodiments, the therapeutic agent is dosed at an amount between about 0.1 mg/kg to about 10 mg/kg, or between about 1 mg/kg to about 5 mg/kg. In embodiments, the therapeutic agent is dosed at an amount between about 10 mg/day to about 100 mg/day. In embodiments, the therapeutic agent is dosed once per day and administered daily for up to 7 days or up to 14 days. In embodiments, the therapeutic agent is dosed by at least one injection either daily or in a single delayed or sustained release injection to provide controlled release of the therapeutic agent.

In embodiments of the methods of preventing BRD in a feedlot, the incidence of BRD is reduced by at least about 50% in the population of cattle. In embodiments, the prevention of BRD results in at least a 50% reduction in antibiotic usage within a facility housing the cattle, or at least a 75% reduction in antibiotic usage within a facility housing the cattle. In embodiments, the incidence of antibiotic resistance is reduced among the population of cattle. In embodiments, the onset of BRD in the cattle is delayed and the mortality is decreased. In embodiments, wherein the cattle having delayed onset of BRD have at least a 50% reduction in antibiotic retreatments. In embodiments, the rectal temperature of the cattle is less than the rectal temperature of a cattle not treated with the therapeutic agent. In embodiments, the therapeutic agent is absent from muscle tissues at three to six weeks post-withdrawal of the drug.

The foregoing summary is illustrative only and is not intended to be in any way limiting. In addition to the illustrative aspects, embodiments, and features described above, further aspects, embodiments, and features will become apparent by reference to the drawings and the following detailed description. Accordingly, the drawings and detailed description are to be regarded as illustrative in nature and not restrictive.

BRIEF DESCRIPTION OF THE DRAWINGS

FIG. 1 shows comparison of clinical parameters (morbidity, mortality, rectal temperature, onset of BRD, and % of retreatments required) between cattle treated with mirtazapine versus no treatment (negative control) as detailed in Example 1.

Various embodiments are described in detail with reference to the drawings, wherein like reference numerals represent like parts throughout the several views. Reference to various embodiments does not limit the scope of the invention. FIGURES represented herein are not limitations to the various embodiments according to the invention and presented for exemplary illustration of the invention.

DETAILED DESCRIPTION OF THE PREFERRED EMBODIMENT

The present invention relates to preventative compositions and methods of employing the same for BRD. The embodiments of this invention are not limited to those methods and compositions disclosed herein, which can vary and are understood by skilled artisans based on the disclosure herein of the present invention. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and moreover may modify the typical measurements referenced herein, and the like. Whether or not modified by the term "about", the claims include equivalents to the quantities.

The term "bovine", as used herein, means a diverse group of medium- to large-sized ungulates, generally having cloven hoofs, and at least one of the sexes having true horns. Bovines include, but are not limited to, domestic cattle.

The term "pharmaceutical agent" or "drug" refers to a chemical compound or composition capable of inducing a desired therapeutic or prophylactic effect when properly administered to a subject.

The term "prevent," "prevention," "metaphylaxis" or "prophylaxis" as referred to herein means the disease (BRD) does not occur in an animal which may be predisposed to the disease or under conditions in which the disease prevalence is high, or that the disease is inhibited, frequency and/or severity is reduced.

The term "prodrug" refers to compounds that are rapidly transformed in vivo to yield the parent compound (mirtazapine), for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference. The term "pharmaceutically acceptable prodrug" as used herein refers to those prodrugs of mirtazapine that are suitable for uses described herein without undue toxicity, irritation, allergic response, and the like, and effective for their intended use.

The term "therapeutically effective amount" (or "effective amount") refers to an amount of an active ingredient, e.g., a therapeutic agent according to the invention, sufficient to effect beneficial or desired results when administered to a subject. An effective amount can be administered in one or more administrations, applications or dosages. A therapeutically effective amount of a composition according to the invention may be readily determined by one of ordinary skill in the art.

The term "veterinarily-acceptable carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

According to an embodiment, methods and compositions for preventing BRD using pre-shipment treatments are provided for cattle. The methods and compositions overcome shortcomings of the conventional vaccine technologies and/or antimicrobial therapies commercially available which are insufficient in preventing BRD. As no broadly effective strategy to combat this disease is currently available, the present invention provides a safe and cost effective anti-BRD drug to reduce this problem and its associated costs. The embodiments described herein provide use of an approved therapeutic agent—namely mirtazapine—as an individually effective prophylactic agents against BRD. Beneficially, the prophylaxis or metaphylaxis of BRD with mirtazapine decreases morbidity, decreases mortality, delays the onset of BRD in cattle populations, and decreases the retreatments required for cattle that develop the BRD. Each of these benefits of the compositions and methods described herein may further beneficially decrease reliance and use of antibiotics as conventionally are administered to most animals. As a further benefit, the reduced usage of unnecessary antibiotics further results in a decrease in antibiotic resistance.

Mirtazapine Compositions and Treatment Methods

The compositions suitable for pre-shipment prophylactic treatments include mirtazapine or its pharmaceutically acceptable derivatives, including salts, solvates, esters, amides, carbamates, or hydrates thereof, in either crystalline or amorphous form. In an embodiment, the salts are preferably pharmaceutically acceptable salts. As referred to herein pharmaceutically acceptable salts can include a salt with an inorganic base, organic base, inorganic acid, organic acid, or basic or acidic amino acid. Examples of inorganic acids for making (pharmaceutically acceptable) salts include hydrochloric, hydrobromic, hydroiodic, nitric, carbonic, sulfuric, and phosphoric acid. Examples of organic acids for making (pharmaceutically acceptable) salts generally include, for example, aliphatic, cycloaliphatic, aromatic, araliphatic, heterocyclic, carboxylic, and sulfonic classes of organic acids.

Mirtazapine, or 6-azamianserin, includes the compound, 1,2,3,4,10,14b-hexahydro-2-methyl-pyrazino[2,1-a]pyrido[2,3-c] benzazepine) in racemic forms. The composition can be provided as a racemic mixture or a pure (or substantially pure) single enantiomer. A single enantiomer can be produced by chiral synthesis or raceinic separation. Non-racemic mixtures of D- and L-racemic forms can also be provided. Mirtazapine has the following chemical formula:

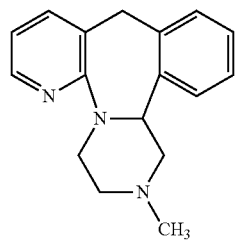 [SMILES: CN1CCN2c3ncccc3Cc3ccccc3C2C1]

Mirtazapine is an FDA-approved active for enhancing appetite in cats (sold under the tradename Mirataz). Mirtazapine is a piperazinoaxepine that acts as a presynaptic alpha-2 antagonist and a postsynaptic serotonergic 5-HT2 and 5-HT3 antagonist conventionally used to treat depression and/or anxiety. It has not previously been known to utilize mirtazapine for BRD prevention.

It is to be understood that the compositions referred to herein may include mirtazapine itself or any pharmaceutically acceptable derivatives, which also include its prodrugs which metabolize to the compound and the analogues and biologically active salt forms thereof, as well as optical isomers which provide the same pharmaceutical results. The mirtazapine is provided in a therapeutically effective amount to prevent BRD, prolong the onset of BRD, and/or decrease the severity of BRD in cattle.

Dosage Forms

Suitable forms for administration of the compounds and compositions described herein (also referred to as the therapeutic agent) that is efficacious against BRD can be prepared for administration in the form of, for example, liquids, powders, aerosols, tablets, capsules, enteric-coated tablets or capsules, or suppositories. The compositions may also include, for example, suspensions, solutions, emulsions in oily or aqueous vehicles, pastes, and implantable sustained-release or biodegradable formulations. In an aspect, compositions include for example, tablets, powder, capsules, solutions (aqueous or non-aqueous), suspensions, syrups, emulsions or inhalable powders or aerosols.

In preferred aspects of the invention, the composition is orally-administered to an animal and therefore the preferred forms for administration include tablets and/or capsules which are dissolved in a solution or solvent, or provided in a solution (aqueous or non-aqueous), syrup, suspensions or emulsion. Such orally-administered dosage forms are preferably food-grade and able to be dosed or provided to an animal or subject with its feed. As the form of the composition may vary a skilled artisan will appreciate the content of the pharmaceutically effective compound will also vary, such as in the range of about 0.1 wt-% to about 90 wt-%, or between about 0.5 wt-% to about 50 wt-% of the oral composition. Such amounts are sufficient to achieve the dosage range specified hereinafter in the methods of the invention.

It is particularly preferable if the composition is administered orally. Suitable oral formulations may be provided in the form of tablets. Further suitable oral formulations may be obtained, for example, by mixing a solid composition (such as a tablet containing the therapeutic agent) with known solvents or diluents such as water or sweetened water. Syrups containing the therapeutic agent according to the invention may additionally contain a sweetener such as saccharine, cyclamate, glycerol or sugar and a flavor enhancer, e.g. a flavoring extract. They may also contain suspension adjuvants or thickeners such as sodium carboxymethyl cellulose, wetting agents such as, for example, condensation products of fatty alcohols with ethylene oxide, or preservatives such as p-hydroxybenzoates as a known in the art of pharmaceutical formulations and compounding.

In other aspects, the composition is administered by injection. The compositions can be made in the form of sterile aqueous solutions or dispersions suitable for injectable use, or made in lyophilized forms using freeze-drying techniques. Such compositions can be made in the form of suspensions or emulsions. In an exemplary embodiment of a formulation for injectable administration, the therapeutic agent is provided in dry (i.e., powder or granular) form for reconstitution with a suitable vehicle (e.g., sterile water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials, such as an emulsion, an ion exchange resin, a sparingly soluble polymer, or a sparingly soluble salt. In an embodiment of the compositions for delivery via injection, the compositions can include a veterinarily-acceptable carrier in a volume of between about 0.1 ml and about 10 ml. In another embodiment the volume of the carrier is between about 0.5 ml and about 5 ml.

Exemplary injected liquids include a carrier. In an embodiment the carrier is constituted by a solvent, such as water, an organic solvent, or a mixture thereof. In an embodiment the solvent is an oil, such as a mixture of an oil and a solvent. Exemplary oils include plant or vegetable oil. Exemplary organic solvents include for example benzyl alcohol, ethanol, N-methyl pyrroli-done, glycerol formate, glycofurol, diethylene glycol mono-ethyl ether, propylene glycol, and polyethylene glycol. In embodiments, the carrier selected should be biocompatible and suitable for the injectable route. The carrier is to be selected from among the polar protic solvents, polar aprotic solvents, apolar aprotic solvents, or the mixture thereof.

The composition preparations of the present invention are manufactured in a manner which is itself well known in the art. For example, the pharmaceutical preparations may be made by means of conventional mixing, granulating, dissolving, lyophilizing processes. The processes to be used will depend ultimately on the physical properties of the active ingredient used.

The compositions for delivering the therapeutic agents can be further co-formulated with additional therapeutic agents, and/or any veterinarily-acceptable carriers and/or adjuvants as conventionally utilized in the prevention of BRD.

Commercially available vaccines may further be combined with the compositions of the invention. In an embodiment, exemplary vaccines that can be combined with the compositions disclosed herein include those for prevention of infections due to *Mannheimia* spp.

Veterinarily-acceptable carriers and/or adjuvants, include for example, any and all solvents, dispersion media, coatings, adjuvants, stabilizing agents, diluents, preservatives, antibacterial and antifungal agents, isotonic agents, adsorption delaying agents, and the like, and can be included in compositions for delivery of the compounds and compositions. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan. The composition may include other pharmaceutically-acceptable excipients for developing powder, liquid or suspension dosage forms, such as disclosed in Remington: The Science and Practice of Pharmacy, Vol. 2, 19th edition (1995), which is hereby incorporated by reference. The amounts and concentrations of carriers, adjuvants and/or additives useful in the compositions of the present invention can readily be determined by the skilled artisan.

Methods of Preventing BRD

The compositions and methods of the invention prevent BRD. In some embodiments, the prevention of BRD is most effective to treat before the time of greatest susceptibility of the animal, i.e., before the animal is shipped to a feedlot from the cow-calf site. It is unexpected that pre-shipment treatments—which are not standard practice for treating cattle—are effective at preventing a disease that has greatest incidence in the feedlot. Although various vaccines are commonly administered to animals at a cow-calf facility, it is desirable and unexpected to identify a pharmacologic (as opposed to vaccine) treatment method to prevent BRD. Moreover, it is unexpected that the delay of the treatment with either mirtazapine at a feedlot does not provide the same efficacy as the methods described herein providing the treatment pre-shipment to the animals. In aspects, there is a decrease in BRD incidence for animals treated before shipment to a feedlot compared to BRD incidence for animals treated only upon arrival at a feedlot. Without being limited to a particular mechanism of action, once an animals arrives at a feedlot, they have undergone stressors during the shipment, which can be travel over a long distance and under conditions they are not accustomed to. The decreased incidence of BRD through the prevention of BRD utilizing compositions and methods described herein can be monitored and measured at a feedlot for the initial 2, 3, 4, 5, 6, or more weeks.

In an embodiment, the animal receives the treatment described herein before leaving the cow-calf site. However, in some embodiments, it may be desired to extend the treatment of the animals after arrival at the feedlot. In a preferred embodiment, the compositions and methods of the invention prevent BRD and/or delay the onset of BRD in the weeks following arrival at a feedlot. This period may be referred to herein as the "stress period" or "period of stress" and refer to the period of time when the respiratory disease occurs most often in the animal.

In an aspect, the methods of the invention focus on treatment of cattle before any animals demonstrate any signs of BRD, or are at greatest risk for developing BRD (i.e. the first 6 weeks at a feedlot), including elevated body temperature (e.g. >102.6° C.), respiratory signs (e.g. nasal discharge, cough, dyspnea, tachypnea), decreased appetite, depression or combinations thereof.

In an aspect, the methods of preventing BRD include administering the therapeutic agent to an animal before shipment to a feedlot. The administering can be in any suitable forms for oral and/or inhaled consumption including for example, tablets, powder, capsules, solutions (aqueous or non-aqueous), suspensions, syrups, emulsions or inhalable powders or aerosols. In some aspects, the composition is administered to the mouth of the animal. In some aspects, the composition is administered into the feed of the animal which is thereafter consumed by the animal.

In other aspects, the methods of preventing BRD include administering the compositions of the invention to an animal in need of such prophylaxis by an injectable form. The administering can be in any suitable forms to be administered directly into the bloodstream, into muscle, or into an internal organ. Suitable means for parenteral administration includes intravenous, intra-arterial, intraperitoneal, intrathecal, intraventricular, intraurethral, intrasternal, intracranial, intramuscular and subcutaneous. Suitable devices for parenteral administration include, for example, needles or microneedles. Parenteral formulations are typically aqueous solutions which can contain excipients and buffering agents (preferably to a pH of from about 3 to about 9, or from about 4 to about 8, or from about 5 to about 7.5, or from about 6 to about 7.5, or about 7 to about 7.5), but for some applications, they can be more suitably formulated as a sterile non-aqueous solution, or as a dried form to be used in conjunction with a suitable vehicle such as sterile water. The preparation of parenteral formulations under sterile conditions, for example, by lyophilisation, can readily be accomplished using standard pharmaceutical techniques well known to those skilled in the art.

In some embodiments for dosing an injection to animals, the therapeutic agent is dosed either daily or in a single delayed or sustained release injection to provide controlled release of the therapeutic agent. As one skilled in the art will ascertain, the injections suitable for veterinary applications can be dissolved in a variety of carriers to provide sustained release, such as for example peanut oil.

In an aspect, the therapeutic agent is administered in a dose of between about 0.1-10 mg/kg/day, or between about 0.1-5 mg/kg/day, between about 0.5-5 mg/kg/day, between about 1-5 mg/kg/day. The dosage rates described herein on a mg/kg basis are understood to refer to the kilogram weight of the animal (i.e. calf). At the time of shipment of cattle to a feedlot the average weight of the cow (which is around 6 months of age) is between about 300 to about 600 pounds. In another aspect, the therapeutic agent mirtazapine is administered in a dose of between about 0.1-10 mg/kg/day, between about 2-8 mg/kg/day, or between about 3-5 mg/kg/day.

In an aspect, the therapeutic agent is administered in a dose of between about 0.1-20 mg/kg/week, or between about 0.1-10 mg/kg/week, or between about 0.5-10 mg/kg/week. In such an embodiment, weekly injections, such as weekly subcutaneous injections may be provided to an animal in need.

In an aspect, the therapeutic agent is administered in a dose of between about 1 mg to 100 mg, between about 10 mg to 100 mg, between about 30 mg to 100 mg, or between about 50 mg to 100 mg, which may be provided in one or more dosages per day to provide the dosage of about 0.1-10 mg/kg/day. In a preferred aspect the dosage is provided on a once a day basis for ease in administration.

In preferred oral dosing embodiments, the therapeutic agent is dosed once per day until the animal is shipped to a feedlot. In some embodiments, the therapeutic agent is dosed once per day for 7 days, or for 10 days, or for 14 days.

In other aspects, it may be preferable to administer a single dose to animals, or, alternatively, two or more injections at a preferred interval. Formulations for parenteral administration can be formulated to be immediate and/or modified release. Extended or controlled release formulations can also be referred to as a long-acting injectable. Modified release formulations include delayed, sustained, pulsed, controlled, targeted, and programmed release. In an aspect, it may be preferable to administer a single dose to animals approximately 3 to 10 days, or 5 to 10 days, or about 7 days before shipment to ensure the mirtazapine is released over time before the shipment and the period of stress that increases the animals' susceptibility to BRD. In some aspects, as a skilled artisan will ascertain based on the selected dosage, rate of administration of the mirtazapine and dosage form, the mirtazapine can be provided in a slowly released dosage for about a week before shipment and remain in the animal's system for up to about a week or more, or up to about 2 weeks or more after shipment.

The therapeutic agents of the invention can be formulated as a solid, semi-solid, or thixotropic liquid for administration as an implanted depot, providing modified release of the active compound. Examples of such formulations include drug-coated stents and poly(dl-lactic-coglycolic) acid (PLGA) microspheres. Those skilled in the art can readily determine the optimal administration regimen.

In an aspect, the methods of preventing BRD include preventing and/or delaying the various clinical signs of BRD such as rhinorrhea, ocular discharge, coughing, dyspnea, anorexia, listlessness, etc. Physical examination of the animals with BRD may exhibit aberrant lung sounds (measured with the stethoscope or the WHISPER device) in combination with the other upper respiratory signs (e.g., rhinorrhea or ocular discharge) plus pyrexia (rectal temperature >102.6° F.) or listlessness or anorexia. According to the methods of prevention described herein, the BRD incidence is significantly lower in the pen of calves receiving the therapeutic agent when compared to the pen receiving a control (or conventional antibiotic and/or vaccine).

According to the invention, the methods of prevention provide at least a 50% reduction in BRD prevalence in treated animals, at least a 60% reduction in BRD prevalence in treated animals, or at least a 70% reduction in BRD prevalence in treated animals.

In some embodiments, where the development of BRD is not prevented, it is significantly delayed and therefore the mortality of the cattle from the BRD is decreased. Without being limited to a particular mechanism of action, the decrease in mortality of the treated cattle is believed to result from the delay in onset of the disease. The longer a cattle are healthy (i.e. not suffering from BRD) it will eat and continue to gain weight, drink fluids, etc. Moreover, as an animal suffers from BRD and it is not feeding it will also lack treatment of other commonly used feedlot therapeutics and feed additives. In an embodiment, the delay in onset of BRD is at least 1 day, 2 days, 3 days, 4 days, 5 days, 6 days, 7 days, 8 days, 9 days, 10 days, or longer. Beneficially, the longer the delay in onset of BRD the better clinical outcomes and reduced mortality that result in the treated cattle.

Beneficially, the methods of prevention significantly reduce the incidence of antibiotic resistance among the treated population of cattle. In an embodiment, the cattle having delayed onset of BRD have at least a 50% reduction in antibiotic retreatments.

In another embodiment, the treated cattle have a lower rectal temperature than the rectal temperature of a cattle not treated with the therapeutic agent.

In an aspect, the therapeutic agent is absent from muscle tissues of the treated animal at three to six weeks post-withdrawal of the drug.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Mirtazapine Treatment

An initial study was performed to confirm BRD prevention at the feedlot using a pre-shipment treatment comprising mirtazapine. A total of 24 ranch heifer calves that were recently weaned (mixed breeds, approximately 350 lbs, 6 months old) were randomly assigned to two different treatment groups. One group was fed mirtazapine in a standard starter feed at 5 mg/kg/day as a pre-shipment treatment. The treatment dosage was extrapolated from feline dosing. After one week, calves were shipped from southern Missouri to Iowa. For the next 4 weeks, calves were monitored for BRD which was ascribed to any animal showing respiratory signs (i.e. coughing, runny nose or eyes, labored or rapid breathing) plus a rectal temperature >104° F. BRD(+) calves were then treated with florfenicol+flunixin. Calves requiring a second treatment received ceftiofur plus tulathromycin, while the third treatment consisted of enrofloxacin, if needed. At the end of the study calves were sold as seedstock and were kept out of the food chain.

The efficacy of the mirtazapine as a pre-shipment treatment for preventing BRD was assessed by various clinical parameters, as shown in Table 1 and FIG. 1.

TABLE 1

|  | None | Mirtazapine | SEM None | SEM Mirtazapine |
|---|---|---|---|---|
| % Morbidity | 84 | 42 | 0 | 0 |
| % Mortality | 7 | 0 | 0 | 0 |
| Avg. Rectal Temp at BRD (degrees F.) | 105.7 | 104.2 | 0.2 | 0.1 |
| Avg. days to onset BRD | 1.5 | 7.3 | 0.2 | 0.5 |
| % Retreats | 55 | 11 | 0 | 0 |

The % morbidity equals the % of calves that developed BRD in the first six weeks. The % mortality equals the percent of BRD(+) calves that died of the disease. The % retreats equals the % of BRD(+) calves that required >2 treatments for BRD once developed. The data are compared to Control calves that were not fed mirtazapine prior to shipping to a feedlot ("None").

Beneficially, the data shows that mirtazapine reduces the morbidity, mortality, and severity (days to onset of BRD and fever response upon clinical presentation with BRD) of BRD when fed to calves for one week prior to shipping (i.e., in vivo).

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein. The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

What is claimed is:

1. A method of preventing bovine respiratory disease (BRD) in a cattle population comprising:
   administering to a population of cattle in need of BRD prevention from about 0.1 mg/kg to about 10 mg/kg of a therapeutic agent comprising mirtazapine or one of its pharmaceutically acceptable derivatives;
   wherein the mirtazapine is administered to the cattle before they are shipped and at a frequency and for a duration of time effective to reduce the incidence of BRD by at least 50%.

2. The method of claim 1, wherein the therapeutic agent is orally-administered.

3. The method of claim 2, wherein the therapeutic agent is provided directly to the mouth of the animal or into the feed source for the animal and the dosage form is a tablet, powder, capsule, aqueous solution, non-aqueous solution, suspension, syrup, or emulsion.

4. The method of claim 1, wherein the therapeutic agent is administered by injection.

5. The method of claim 4, wherein the injection is in the form of a thixotropic liquid.

6. The method of claim 4, wherein the injection provides an implanted depot to provide modified release of the mirtazapine.

7. The method of claim 1, wherein the therapeutic agent is dosed at an amount between about 1 mg/kg to about 5 mg/kg.

8. The method of claim 1, wherein the therapeutic agent is dosed once per day and administered daily for up to 7 days or up to 14 days.

9. The method of claim 1, wherein the therapeutic agent is dosed by at least one injection either daily or in a single delayed or sustained release injection to provide controlled release of the therapeutic agent.

10. The method of claim 1, wherein the prevention of BRD results in at least a 50% reduction in antibiotic usage within a facility housing the cattle.

11. The method of claim 10, wherein the prevention of BRD results in at least a 75% reduction in antibiotic usage within a facility housing the cattle.

12. The method of claim 10, wherein the incidence of antibiotic resistance is reduced among the population of cattle.

13. The method of claim 1, wherein the onset of BRD in the cattle is delayed and the mortality is decreased.

14. The method of claim 13, wherein the cattle having delayed onset of BRD have at least a 50% reduction in antibiotic retreatments.

15. The method of claim 1, wherein the rectal temperature of the cattle is less than the rectal temperature of a cattle not treated with the therapeutic agent.

16. The method of claim 1, wherein the therapeutic agent is absent from muscle tissues at three to six weeks post-withdrawal of the drug.

* * * * *